US012599627B1

(12) United States Patent
Abdulkhair et al.

(10) Patent No.: US 12,599,627 B1
(45) Date of Patent: Apr. 14, 2026

(54) METHOD OF TREATING CANCER CELLS USING COPPER HYDROXIDE NITRATE/CALCIUM SILICATE/GRAPHITIC CARBON NITRIDE NANOCOMPOSITE MATERIAL

(71) Applicant: IMAM MOHAMMAD IBN SAUD ISLAMIC UNIVERSITY, Riyadh (SA)

(72) Inventors: Babiker Yagoub Elhadi Abdulkhair, Riyadh (SA); Mohamed Khairy Abdel Fattah Omran, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/224,367

(22) Filed: May 30, 2025

(51) Int. Cl.
*A61K 33/34* (2006.01)
*C12N 5/09* (2010.01)
*B82Y 5/00* (2011.01)
*B82Y 40/00* (2011.01)

(52) U.S. Cl.
CPC ............ *A61K 33/34* (2013.01); *C12N 5/0693* (2013.01); *B82Y 5/00* (2013.01); *B82Y 40/00* (2013.01)

(58) Field of Classification Search
CPC ........... A61K 33/34; B82Y 5/00; B82Y 40/00
See application file for complete search history.

(56) References Cited

U.S. PATENT DOCUMENTS

| | | | | |
|---|---|---|---|---|
| 12,350,291 B1* | 7/2025 | Omran | ..................... | A61K 9/16 |
| 12,364,711 B1* | 7/2025 | Omran | .................. | A61K 33/08 |
| 12,370,213 B1* | 7/2025 | Omran | .................. | A61P 35/00 |
| 12,370,215 B1* | 7/2025 | Omran | .................. | A61K 33/08 |
| 12,419,911 B1* | 9/2025 | Omran | .................. | A61K 33/24 |

FOREIGN PATENT DOCUMENTS

| | | |
|---|---|---|
| CN | 117717631 A | 3/2024 |
| IN | 202311022975 A | 10/2024 |

OTHER PUBLICATIONS

Hamidreza Abdouss, et al., "Green synthesis of chitosan/polyacrylic acid/graphitic carbon nitride nanocarrier as a potential pH-sensitive system for curcumin delivery to MCF-7 breast cancer cells", International Journal of Biological Macromolecules, vol. 242, Part 3, May 25, 2025, 125134, pp. 1-14.

(Continued)

*Primary Examiner* — Carlos A Azpuru

(74) *Attorney, Agent, or Firm* — Oblon, McClelland, Maier & Neustadt, L.L.P.

(57) ABSTRACT

A method of inhibiting a cancer cell growth includes contacting the cancer cell with a $Cu_2(OH)_3NO_3/CaSiO_3$@g-$C_3N_4$ nanocomposite material containing graphitic carbon nitride (g-$C_3N_4$), copper hydroxide nitrate ($Cu_2(OH)_3NO_3$) and calcium silicate ($CaSiO_3$), achieving an inhibition efficiency on human breast carcinoma (MCF-7) and human hepatocellular carcinoma (HepG-2) cell growth of greater than 95% in an in-vitro cellular viability assay.

19 Claims, 4 Drawing Sheets

50

Mix a calcium silicate ($CaSiO_3$), a graphite-phase carbon nitride (g-$C_3N_4$), and a copper salt in a glycol solvent to form a mixture ⎯ 52

Microwave the mixture to form the $Cu_2(OH)_3NO_3/CaSiO_3$@g-$C_3N_4$ nanocomposite ⎯ 54

(56)           References Cited

OTHER PUBLICATIONS

Pranjyan Dash, et al., "Near-infrared driven gold nanoparticles-decorated g-c3n4/sns2 heterostructure through photodynamic and photothermal therapy for cancer treatment", International Journal of Nanomedicine, vol. 19, Oct. 17, 2024, pp. 10537-10550.
Mengjiao Zhang, et al., "Different effects of a novel CaO—MgO—SiO2-based multiphase glass-ceramic on cell behaviors of normal and cancer cells in vitro", Colloids and Surfaces B: Biointerfaces, vol. 116, Apr. 1, 2014, pp. 1-8 (accepted manuscript).

* cited by examiner

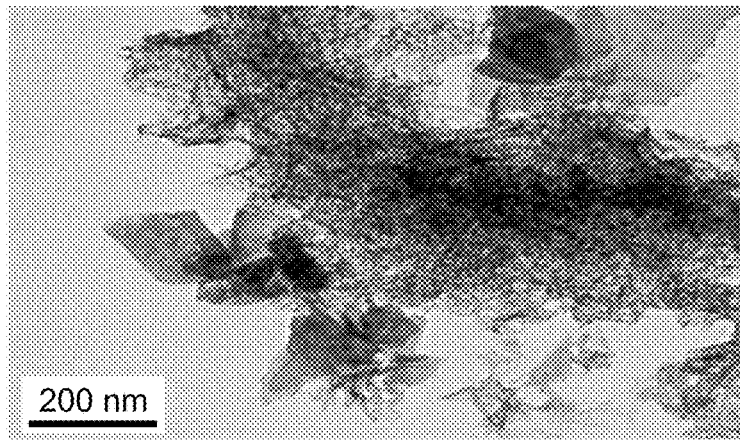
FIG. 3A
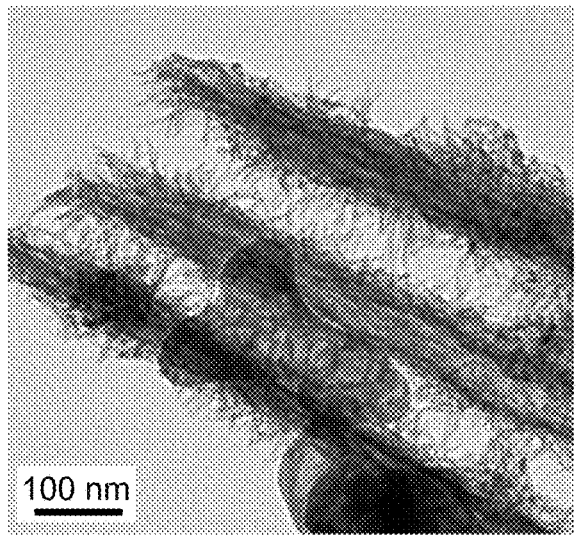
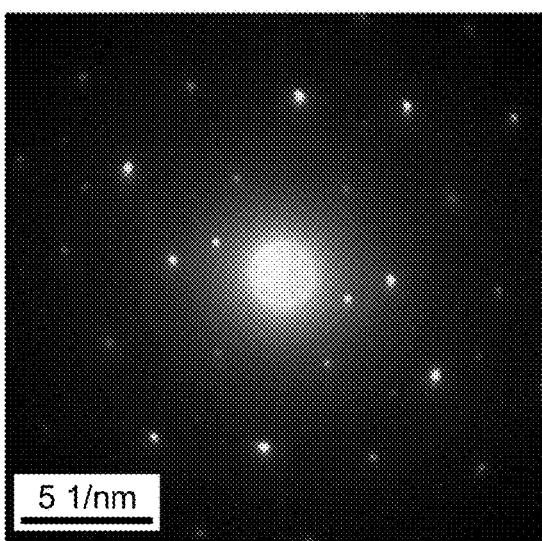
FIG. 3B                    FIG. 3C

METHOD OF TREATING CANCER CELLS USING COPPER HYDROXIDE NITRATE/CALCIUM SILICATE/GRAPHITIC CARBON NITRIDE NANOCOMPOSITE MATERIAL

BACKGROUND

Technical Field

The present disclosure is related to a method of treating cancer cells to inhibit cancer cell growth. The present disclosure is also related to contacting the cancer cells with a nanocomposite material. More particularly, the present disclosure is related to a nanocomposite material including copper hydroxide nitrate ($Cu_2(OH)_3NO_3$), calcium silicate ($CaSiO_3$), and graphite-phase carbon nitride (g-$C_3N_4$).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer is the leading cause of death and disability worldwide due to its complicated pathological process. A conventional method for cancer treament is chemotherapy, which suffers numerous challenges including cytotoxicity, low therapeutic indices, low bioavailability, insolubility, high dose requirements, non-specific targeting, and the development of multiple drug resistance. In particular, cancer treament may result in resistance from overexpression of drug efflux transporters, development of anoxic conditions, and deviation towards abnormal apoptotic pathways. To address these challenges, many nanomaterials (NMs) have gained interest as a promising candidate of anticancer agents [See: Mandal, A. K., *Nanomaterials as targeted delivery system of therapeutics for inhibition of cancer. Journal of Drug Delivery and Therapeutics,* 2023. 13(12): p. 201-223; and Algethami, F. K., et al., *Fast fabrication of bismuth oxyiodide/carbon-nanofibers composites for efficient antiproliferation of liver and breast cancer cells. Zeitschrift für anorganische und allgemeine Chemie,* 2021. 647(19): p. 1921-1929]. Size, shape, and surface optimization of NMs improves the targeting efficiency and the circulation time, which in turn increases the targeting potential of anticancer cargos. The NMs can boost therapeutic efficacy by controlled release by targeting cargos to cancer sites through encapsulation or coupling with ligands. In cancer treatment, NMs are often used to target cancer cells, tumor microenvironment, and immune system primarily through stimuli-responsive targeting or by modifying their surfaces with targeting ligands like transferin, integrins, sugar, folic acid, and antibodies to improve tissue targeting recognition and internalization.

Although several nanomaterials have been used in the past for cancer treatment, there still exisits the necessity to develop nanomaterials with improved selectivity and cytotoxic activity against cancer cells.

SUMMARY

One aspect of the present disclosure is a method of inhibiting a cancer cell growth. The method may include contacting a $Cu_2(OH)_3NO_3/CaSiO_3$@g-$C_3N_4$ nanocomposite with a cancer cell such that the cancer cell grows on the Cu2(OH)3NO3/CaSiO3@g-C3N4 nanocomposite. The method may further include inhibiting the cancer cell growth on the $Cu_2(OH)_3NO_3/CaSiO_3$@g-$C_3N_4$ nanocomposite.

In a further embodiment, the method may include contacting the cancer cell with the $Cu_2(OH)_3NO_3/CaSiO_3$@g-$C_3N_4$ nanocomposite at a certain minimum concentration.

In a further embodiment, the $Cu_2(OH)_3NO_3/CaSiO_3$@g-$C_3N_4$ nanocomposite may include a graphite-phase carbon nitride (g-$C_3N_4$), a copper hydroxide nitrate ($Cu_2(OH)_3NO_3$) and a calcium silicate ($CaSiO_3$).

In a further embodiment, the cancer cell may be a cell line selected from a group consisting of a human hepatocellular carcinoma (HepG-2) cell line and a human breast carcinoma (MCF-7) cell line.

In a further embodiment, the $Cu_2(OH)_3NO_3/CaSiO_3$@g-$C_3N_4$ nanocomposite may have a certain half-maximal inhibitory concentration ($IC_{50}$) value for the HepG-2 cell line.

In a further embodiment, the $Cu_2(OH)_3NO_3/CaSiO_3$@g-$C_3N_4$ nanocomposite may have a certain half-maximal inhibitory concentration ($IC_{50}$) value for the MCF-7 cell line.

Another aspect of the present disclosure includes a process to make the $Cu_2(OH)_3NO_3/CaSiO_3$@g-$C_3N_4$ nanocomposite. The process may include mixing a $CaSiO_3$, a g-$C_3N_4$, and a copper salt in a glycol solvent to form a mixture, followed by microwaving the mixture to form the $Cu_2(OH)_3NO_3/CaSiO_3$@g-$C_3N_4$ nanocomposite.

In a further embodiment, the $CaSiO_3$ may be formed by sonicating a mixture of a calcium salt and a silicate salt in an aqueous alcohol solution to form a $CaSiO_3$ mixture, followed by heating the $CaSiO_3$ mixture to an elevated temperature for a sufficient amount of time to form the $CaSiO_3$.

In a further embodiment, the calcium salt may be selected from a group consisting of calcium nitrate ($Ca(NO_3)_2$), calcium chloride ($CaCl_2$), calcium phosphate ($Ca_3(PO_4)_2$), calcium carbonate ($CaCO_3$) and calcium citrate ($C_{12}H_{10}Ca_3O$), and the silicate salt may be selected from a group consisting of calcium silicate ($Ca_2O_4Si$), sodium silicate ($Na_2SiO_3$), potassium silicate ($K_2O_5Si_3$), zeolites and micas.

In a further embodiment, the g-$C_3N_4$ may be formed by heating urea to an elevated temperature for a sufficient amount of time.

In a further embodiment, the mixing may include a copper salt selected from a group consisting of copper nitrate ($Cu(NO_3)_2$), copper chloride($CuCl_2$), copper sulfate ($CuSO_4$), copper bromide (CuBr), and copper cyanide (CuCN).

In a further embodiment, the method of microwaving the mixture may be performed at an elevated temperature under a certain pressure for a sufficient amount of time.

In a further embodiment, the $Cu_2(OH)_3NO_3/CaSiO_3$@g-$C_3N_4$ nanocomposite may include a plurality of metal oxide nanorods and a plurality of g-$C_3N_4$ nanosheets.

In a further embodiment, the $Cu_2(OH)_3NO_3/CaSiO_3$@g-$C_3N_4$ nanocomposite may have the metal oxide nanorods, including $Cu_2(OH)_3NO_3$ and $CaSiO_3$.

In a further embodiment, the $Cu_2(OH)_3NO_3/CaSiO_3$@g-$C_3N_4$ nanocomposite may have the metal oxide nanorods of a certain average length.

In a further embodiment, the $Cu_2(OH)_3NO_3/CaSiO_3$@g-$C_3N_4$ nanocomposite may have the metal oxide nanorods includes nanowires protruding perpendicularly to the rods.

In a further embodiment, the $Cu_2(OH)_3NO_3/CaSiO_3@g$-$C_3N_4$ nanocomposite may have the metal oxide nanorods including nanowires of a certain length dispersed on the g-$C_3N_4$ nanosheets with some aggregates of the metal oxide nanorods.

In a further embodiment, the $Cu_2(OH)_3NO_3/CaSiO_3@g$-$C_3N_4$ nanocomposite may have a mesoporous structure with a plurality of wide pores in the g-$C_3N_4$ nanosheets where the metal oxide nanorods deposit.

In a further embodiment, the $Cu_2(OH)_3NO_3/CaSiO_3@g$-$C_3N_4$ nanocomposite may have a certain average pore diameter.

In a further embodiment, the $Cu_2(OH)_3NO_3/CaSiO_3@g$-$C_3N_4$ nanocomposite may have a certain Brunauer-Emmett-Teller (BET) surface area.

In a further embodiment, the $Cu_2(OH)_3NO_3/CaSiO_3@g$-$C_3N_4$ nanocomposite may have a certain average pore volume.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 3A shows a transmission electron microscopy (TEM) image of the $Cu_2(OH)_2NO_3/CaSiO_3@g$-$C_3N_4$ nanocomposite at 200 nanometers (nm) scale, according to certain embodiments.

FIG. 3B shows a TEM image of the $Cu_2(OH)_2NO_3/CaSiO_3@g$-$C_3N_4$ nanocomposite at 100 nm scale, according to certain embodiments.

FIG. 3C shows a selected area electron diffraction (SAED) pattern of the $Cu_2(OH)_2NO_3/CaSiO_3@g$-$C_3N_4$ nanocomposite, according to certain embodiments.

DETAILED DESCRIPTION

Figure 1:
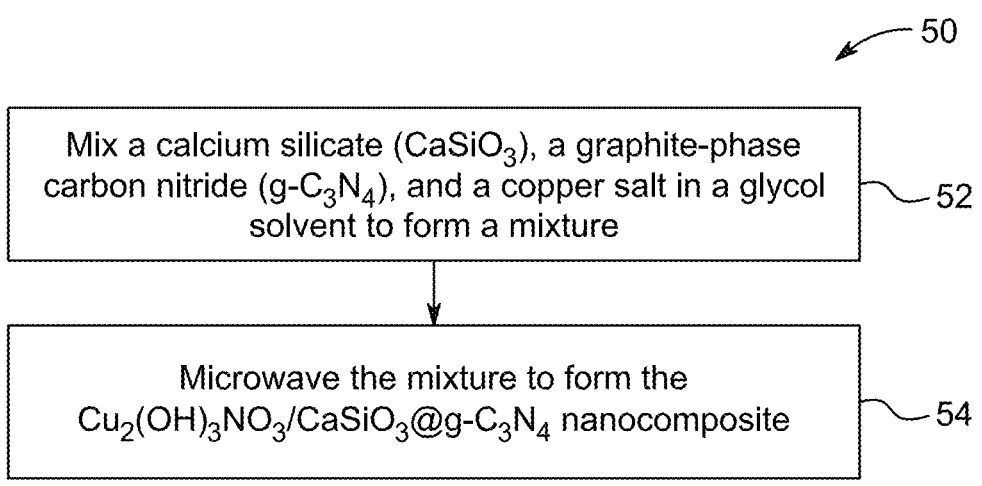
FIG. 1 is an exemplary flowchart of the method of formation of $Cu_2(OH)_2NO_3/CaSiO_3@g$-$C_3N_4$ nanocomposite, according to certain embodiments.

Embodiments of the present invention will now be described fully hereinafter with reference to the accompanying drawings wherever applicable, in that some, but not all, embodiments of the disclosure are shown.

In the drawings, like reference numerals designate identical or corresponding parts throughout the several views.

Further, as used herein, the words "a", "an" and the like generally carry a meaning of "one or more", unless stated otherwise.

When describing the present disclosure, the terms used are to be construed in accordance with the following definitions, unless a context dictates otherwise.

Furthermore, the terms 'approximately,' 'approximate,' 'about,' and similar terms generally refer to ranges that include the identified value within a margin of 20 percent (%), 10%, or preferably 5%, and any values therebetween.

When amounts, concentrations, dimensions, and other parameters are expressed in the form of a range, a preferable range, an upper limit value, a lower limit value, or preferable upper and limit values, it should be understood that any ranges obtainable by combining any upper limit or preferable value with any lower limit or preferable value are also specifically disclosed, irrespective of whether the obtained ranges are clearly mentioned in the context.

In this disclosure, a numerical value interval (i.e., a numerical value range) is involved, and, if not specifically stated, an optional numerical value distribution is considered continuous within the numerical value interval and includes two numerical value endpoints (i.e., minimum and maximum values) of the numerical value range and each numerical value between the two numerical value endpoints.

The temperature parameters in the present disclosure, if not specifically limited, are both allowed to be constant temperature processing and allowed to be varied within a certain temperature interval. It should be understood that the constant temperature processing allows the temperature to fluctuate within the precision range of the instrument control. It is allowed to fluctuate in the range of, for example, $5°$ C., $4°$ C., $3°$ C., $2°$ C., $1°$ C.

A weight percent of a component, unless specifically stated to the contrary, is based on the total weight of the formulation or composition in which the component is included. For example, if a particular element or component in a composition or article is said to have 5 weight percent (wt. %), it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopes of nitrogen include $^{14}N$ and $^{15}N$. Isotopes of Ca include $^{40}Ca$, $^{42}Ca$, $^{43}Ca$, $^{44}Ca$, and $^{46}Ca$. Isotopes of silicon include $^{28}Si$, $^{29}Si$, and $^{30}Si$. Isotopes of hydrogen include $^{1}H$, $^{2}H$, and $^{3}H$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the term 'pharmaceutical composition' refers to a mixture of the compounds described herein or pharmaceutically acceptable salts, esters, or prodrugs thereof, with other chemical components, such as physiologically acceptable carriers and excipients.

As used herein, the term 'cancer' refers to all types of cancer, neoplasm, or malignant tumors found in mammals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such teens may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with, a pathology related to or caused in part by unregulated or aberrant cellular division, (4) an increase: in disease-free, relapse-free, progression-free, and/or overall survival, duration, or rate (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

Aspects of the present disclosure are directed to a method of treating cancer using a nanocomposite material including copper hydroxide nitrate $(Cu_2(OH)_3NO_3)$, calcium silicate $(CaSiO_3)$, and graphitic-phase carbon nitride $(g\text{-}C_3N_4)$. When each component of the nanocomposite material is used in appropriate ratios, the contact of the nanocomposite material with cancer cells can effectively inhibit cancer cell growth.

A $Cu_2(OH)_3NO_3/CaSiO_3@g\text{-}C_3N_4$ nanocomposite (also referred to as a nanocomposite) is described. The nanocomposite includes a copper hydroxide nitrate $(Cu_2(OH)_3NO_3)$ and a calcium silicate $(CaSiO_3)$ based nanocomposite dispersed on a matrix of a graphite-phase carbon nitride $(g\text{-}C_3N_4)$. In some embodiments, the graphite-phase carbon nitride $(g\text{-}C_3N_4)$ is present in an amount of 5 to 10 percent by weight (wt. %), preferably 10 to 15 wt. %, more preferably 15 to 20 percent wt. % based on the total weight of the nanocomposite. In a preferred embodiment, a graphite-phase carbon nitride $(g\text{-}C_3N_4)$ is present in an amount of 20 to 40 wt. %. based on the total weight of the nanocomposite.

In some embodiments, the copper hydroxide nitrate $(Cu_2(OH)_3NO_3)$ is present in an amount of 5 to 10 percent by weight (wt. %), preferably 10 to 15 wt. %, more preferably 15 to 20 percent wt. % based on the total weight of the nanocomposite. In a preferred embodiment, the copper hydroxide nitrate $(Cu_2(OH)_3NO_3)$ is present in an amount of 20 to 40 wt. %. based on the total weight of the nanocomposite.

In some embodiments, the calcium silicate $(CaSiO_3)$ in an amount of 20 to 40 wt. %, is present in an amount of 5 to 10 percent by weight (wt. %), preferably 10 to 15 wt. %, more preferably 15 to 20 percent wt. % based on the total weight of the nanocomposite. In a preferred embodiment, a graphite-phase carbon nitride $(g\text{-}C_3N_4)$ is present in an amount of 20 to 40 wt. %. based on the total weight of the nanocomposite.

In some embodiments, the nanocomposite is porous. A porous material is one that forms a porous bulk solid. Pores may be micropores, mesopores, macropores, and/or a combination thereof. The pores exist in the bulk material, not necessarily in the molecular structure of the material. The term 'microporous' means that nanocomposites have pores with an average pore width (i.e., diameter) of less than 2 nm. The term 'mesoporous' means the pores of the nanocomposite have an average pore width of 2-50 nm. The term 'macroporous' means the pores of the nanocomposite have an average pore width larger than 50 nm. Pore size may be determined by methods including, but not limited to, gas adsorption (e.g., $N_2$ adsorption), imaging techniques such as scanning electron microscopy (SEM) and transmission electron microscopy (TEM). In a preferred embodiment, the $Cu_2(OH)_3NO_3/CaSiO_3@g\text{-}C_3N_4$ nanocomposite has a mesoporous structure with a plurality of wide pores in the $g\text{-}C_3N_4$ nanosheets where the metal oxide nanorods deposit.

A Brunauer-Emmett-Teller (BET) specific surface area of the nanocomposite is in a range of from 10-40 square meters per gram $(m^2/g)$, preferably 40-60 $m^2/g$, preferably 45-65 $m^2/g$, preferably 60-80 $m^2/g$, preferably 65-85 $m^2/g$, preferably 85-105 $m^2/g$, preferably 115-125 $m^2/g$, preferably 125-145 m$^2$/g, and preferably 135-165 m$^2$/g. In a preferred embodiment, the Cu$_2$(OH)$_3$NO$_3$/CaSiO$_3$@g-C$_3$N$_4$ nanocomposite has a Brunauer-Emmett-Teller (BET) surface area of 140 to 160 m$^2$·g$^{-1}$. The BET hypothesis is the foundation for a significant analysis method for determining the specific surface area of a material. It attempts to explain the physical adsorption of gas molecules on a solid surface. Specific surface area is a property of solids, which is the total surface area of a material per unit of mass, solid or bulk volume, or cross-sectional area. The marked high specific surface area reflects the good dispersion of the metal oxide nanoparticles on the g-C$_3$N$_4$. and the CaSiO$_3$. In some embodiments, pore diameter, pore volume, and BET surface area are measured by gas adsorption analysis, preferably N$_2$ adsorption analysis (e.g., N$_2$ adsorption isotherms).

An average pore volume of the nanocomposite, according to the Barrett-Joyner-Halenda (BJH) measurement method, is in a range of from 0.06 to 0.12 cubic centimeter per gram (cm$^3$/g), preferably 0.07 to 0.11 cm$^3$/g, preferably 0.08 to 0.10 cm$^3$/g, and preferably 0.09 cm$^3$/g. In a preferred embodiment, the Cu$_2$(OH)$_3$NO$_3$/CaSiO$_3$@g-C$_3$N$_4$ nanocomposite has an average pore volume of 0.3 to 0.4 cm$^3$·g$^{-1}$.

An average pore diameter of the nanocomposite, according to the BJH measurement method, is in a range of 10 to 15 nm, preferably 9 to 14 nm, preferably 8 to 12 nm, and more preferably 7 to 10 nm. In a preferred embodiment, according to the BJH measurement method, the Cu$_2$(OH)$_3$NO$_3$/CaSiO$_3$@g-C$_3$N$_4$ nanocomposite material has an average pore diameter of from about 3 to 7 nm.

In a preferred embodiment, the Cu$_2$(OH)$_3$NO$_3$/CaSiO$_3$@g-C$_3$N$_4$ nanocomposite includes a plurality of metal oxide nanorods and a plurality of g-C$_3$N$_4$ nanosheets. In another preferred embodiment, the Cu$_2$(OH)$_3$NO$_3$/CaSiO$_3$@g-C$_3$N$_4$ nanocomposite has the metal oxide nanorods, including the Cu$_2$(OH)$_3$NO$_3$ and the CaSiO$_3$.

In some embodiments, the Cu$_2$(OH)$_3$NO$_3$/CaSiO$_3$@g-C$_3$N$_4$ nanocomposite has the metal oxide nanorods of an average length of 0.5 to 0.8 micrometers (μm), preferably 0.8 to 1 μm, and more preferably 1 to 2 μm. In a preferred embodiment, the Cu$_2$(OH)$_3$NO$_3$/CaSiO$_3$@g-C$_3$N$_4$ nanocomposite has the metal oxide nanorods of an average length of 1 to 3 μm.

In some embodiments, the Cu$_2$(OH)$_3$NO$_3$/CaSiO$_3$@g-C$_3$N$_4$ nanocomposite has the metal oxide nanorods, including nanowires of a length 1 to 3 nm, dispersed on the g-C$_3$N$_4$ nanosheets, preferably length 4 to 8 nm, and more preferably 4 to 10 nm. In a preferred embodiment, the Cu$_2$(OH)$_3$NO$_3$/CaSiO$_3$@g-C$_3$N$_4$ nanocomposite has the metal oxide nanorods including nanowires of a length of 10 to 50 nm, dispersed on the g-C$_3$N$_4$ nanosheets.

In a preferred embodiment, the Cu$_2$(OH)$_3$NO$_3$/CaSiO$_3$@g-C$_3$N$_4$ nanocomposite has some aggregates of the metal oxide nanorods dispersed on the g-C$_3$N$_4$ nanosheet. The metal oxide nanorods in the Cu$_2$(OH)$_3$NO$_3$/CaSiO$_3$@g-C$_3$N$_4$ nanocomposite may exhibit various arrangements on the g-C$_3$N$_4$ nanosheets. These include uniformly dispersed individual rods, clustered aggregates, oriented arrays aligned in a specific direction, randomly oriented rods, interwoven or cross-linked networks, or vertically aligned rods standing on the nanosheet surface. Each configuration may influence charge transfer efficiency and active surface exposure.

According to another aspect of the present disclosure, a method of making the Cu$_2$(OH)$_3$NO$_3$/CaSiO$_3$@g-C$_3$N$_4$ nanocomposite material is described (FIG. 1). The order in which the method 50 is described is not intended to be construed as a limitation, and any number of the method steps described may be combined to implement the method 50. Additionally, individual steps may be removed or skipped from method 50 without departing from the spirit and scope of the present disclosure.

At step 52, the method 50 includes mixing a calcium silicate (CaSiO$_3$), a graphite-phase carbon nitride (g-C$_3$N$_4$), and a copper salt in a glycol solvent to form a mixture. The mixture refers to a homogeneous suspension or dispersion containing the calcium silicate (CaSiO$_3$), the graphite-phase carbon nitride (g-C$_3$N$_4$), and the copper salt uniformly combined in the glycol solvent, serving as the precursor for nanocomposite formation.

In some embodiments, the calcium silicate is formed by sonicating a mixture of a calcium salt and a silicate salt in an aqueous alcohol solution to form a calcium silicate mixture and heating the calcium silicate mixture to a temperature of 160 to 200° C. for 1 to 3 hours (h) to form the CaSiO$_3$.

In some embodiments, the calcium salt is selected from calcium nitrate, calcium chloride, calcium phosphate, calcium carbonate, and calcium citrate. In a preferred embodiment, the calcium salt is calcium nitrate. In some embodiments, the silicate salt is at least one selected from potassium silicate, lithium silicate, rubidium silicate, cesium silicate, sodium orthosilicate, potassium orthosilicate, lithium orthosilicate, rubidium orthosilicate, cesium orthosilicate, sodium disilicate, potassium disilicate, lithium disilicate, rubidium disilicate, cesium disilicate, sodium trisilicate, potassium trisilicate, lithium trisilicate, rubidium trisilicate, cesium trisilicate, sodium tetrasilicate, potassium tetrasilicate, lithium tetrasilicate, rubidium tetrasilicate, cesium tetrasilicate, sodium hexasilicate, potassium hexasilicate, lithium hexasilicate, rubidium hexasilicate, and cesium hexasilicate. In some embodiments, the silicate salt is selected from a group consisting of calcium silicate, sodium silicate, potassium silicate, zeolites, and micas. In a preferred embodiment, the silicate salt is sodium metasilicate.

In some embodiments, the aqueous alcohol solution may include at least one alcohol selected from methanol, propanol, isopropanol, butanol, isobutanol, sec-butanol, tert-butanol, 1-propanol, 2-propanol, 1-butanol, 2-butanol, methylpropanol, dimethylpropanol, ethylpropanol, cyclopropanol, fluoromethanol, chloromethanol, bromomethanol, and iodomethanol. In a preferred embodiment, equal moles of calcium nitrate and sodium metasilicate were dispersed in 100 ml of ethanol:water (1:1). Water may be tap water, distilled water, double-distilled water, deionized water, deionized distilled water, reverse osmosis water, and/or some other water.

In some embodiments, the calcium silicate mixture can be heated using heating appliances such as ovens, microwaves, autoclaves, hot plates, heating mantles and tapes, oil baths, salt baths, sand baths, air baths, hot-tube furnaces, and hot-air guns.

In some embodiments, the calcium silicate mixture is heated at a temperature of from 160-200° C., preferably 161-198° C., preferably 162-197° C., preferably 163-196° C., preferably 164-195° C., preferably 165-194° C., preferably 166-193° C., preferably 167-192° C., preferably 168-191° C., preferably 169-190° C., preferably 170-189° C., preferably 171-187° C., preferably 172-188° C., preferably 173-187° C., preferably 174-186° C., preferably 175-185° C., preferably 176-184° C., preferably 177-183° C., preferably 178-182° C., preferably 179-181° C., for 1-3 h, preferably 1.1-2.9 h, preferably 1.2-2.8 h, preferably 1.3-2.7 h, preferably 1.4-2.6 h, preferably 1.5-2.5 h, preferably 1.6-2.4 h, preferably 1.7-2.3 h, preferably 1.8-2.2 h, preferably 1.9-2.1 h to form the $CaSiO_3$. In a preferred embodiment, the mixture is transferred in an autoclave and heated at 180° C. for 2 h in an oven.

In some embodiments, the g-$C_3N_4$ is formed by heating urea to a temperature of 550 to 650° C., preferably 555-645° C., preferably 560-640° C., preferably 565-635° C., preferably 570-630° C., preferably 575-625° C., preferably 580-620° C., preferably 585-615° C., preferably 590-610° C., preferably 595-605° C. for 30-60 min, preferably 31-59 min, preferably 32-58 min, preferably 33-57 min, preferably 34-56 min, preferably 35-55 min, preferably 36-54 min, preferably 37-53 min, preferably 38-52 min, preferably 39-51 min, preferably 40-50 min, preferably 41-49 min, preferably 42-48 min, preferably 43-47 min, preferably 44-46 min. In a preferred embodiment, the urea is heated at 600° C. for 45 min.

In an alternate embodiment, other nitrogen-containing precursors, to urea, such as melamine, dicyandiamide, ammonium thiocyanate, or ammonium carbonate, may also be used. These alternatives provide nitrogen necessary for the formation of carbon nitride structures. Typically, these precursors are used in amounts of approximately 5 wt. % relative to the total weight of the nanocomposite to achieve the desired nitrogen content for the desired structural properties.

In some embodiments, the copper salt is selected from a group consisting of copper nitrate, copper chloride, copper sulfate, copper bromide, and copper cyanide.

In some embodiments, the $Cu_2(OH)_3NO_3/CaSiO_3@g$-$C_3N_4$ nanostructure includes $Cu_2(OH)_3NO_3$, $CaSiO_3$, and g-$C_3N_4$ in a mass ratio of 0.5-1.5:0.5-1.5:0.5-1.5, preferably 0.6-1.4:0.6-1.4:0.6-1.4, preferably 0.7-1.3:0.7-1.3:0.7-1.3, and preferably 0.8-1.2:0.8-1.2:0.8-1.2, preferably 0.9-1.1:0.9-1.1:0.9-1.1 in a preferred embodiment, the mass ratio of $Cu_2(OH)_3NO_3$, $CaSiO_3$, and g-$C_3N_4$ is 1:1:1.

At step 54, the method 50 includes microwaving the mixture to form the $Cu_2(OH)_3NO_3/CaSiO_3@g$-$C_3N_4$ nanocomposite. In some embodiments, the mixture is microwaved at a temperature of 160-200° C., preferably 161-199° C., preferably 163-197° C., preferably 165-195° C., preferably 167-193° C., preferably 169-191° C., preferably 171-189° C., preferably 173-187° C., preferably 175-185° C., preferably 177-183° C., preferably 178-182° C., preferably 179-181° C., at a pressure of 4 to 6 bar, preferably 4.1-5.9 bar, preferably 4.2-5.8 bar, preferably 4.3-5.7 bar, preferably 4.4-5.6 bar, preferably 4.5-5.5 bar, preferably 4.6-5.4 bar, preferably 4.7-5.3 bar, preferably 4.8-5.2 bar, preferably 4.9-5.1 bar, for 30-90 min, preferably 31-89 min, preferably 33-87 min, preferably 36-85 min, preferably 39-83 min, preferably 41-81 min, preferably 43-79 min, preferably 46-77 min, preferably 49-75 min, preferably 52-73 min, preferably 55-70 min, preferably 57-68 min, preferably 59-65 min. In a preferred embodiment, the mixture is microwaved at 180° C. and 5.0 bar pressure for 60 min to form the nanocomposite.

Another aspect of the present disclosure is a method of treating cancer cells using the nanocomposite. In some embodiments, the cancer cell is from a cell line selected from a group consisting of a human hepatocellular carcinoma (HepG-2) cell line and a human breast carcinoma (MCF-7) cell line.

The method includes contacting the cancer cell with the $Cu_2(OH)_3NO_3/CaSiO_3@g$-$C_3N_4$ nanocomposite at a concentration in a range of 3 to 500 micrograms per millilitres (μg/mL), preferably 6 to 497 μg/mL, preferably 15-485 μg/mL, preferably 30 to 470 μg/mL, preferably 60 to 440 μg/mL, preferably 90 to 410 μg/mL, preferably 120 to 380

μg/mL, preferably 150 to 350 μg/mL, preferably 180 to 320 μg/mL, preferably 210 to 290 μg/mL.

Contacting the cancer cell results in inhibiting the cancer cell growth on the $Cu_2(OH)_3NO_3/CaSiO_3@g$-$C_3N_4$ nanocomposite. In some embodiments, the nanocomposite material has a half-maximal inhibitory concentration ($IC_{50}$) value for Human Hepatocellular Carcinoma (HepG-2) cells in the range of 5 to 15 μg/mL, preferably 6 to 14 μg/mL, preferably 7 to 13 μg/mL, preferably 8 to 12 μg/mL, and preferably 9 to 11 μg/mL. In a preferred embodiment, the $Cu_2(OH)_3NO_3/CaSiO_3@g$-$C_3N_4$ nanocomposite material has an $IC_{50}$ value of 9.42 μg/mL in an in-vitro cellular viability assay.

In some embodiments, the nanocomposite material has a $IC_{50}$ value for human Breast carcinoma (MCF-7) cells in the range of 20 to 30 μg/mL, preferably 21 to 29 μg/mL, preferably 22 to 28 μg/mL, and preferably 24 to 26 μg/mL. In a preferred embodiment, the nanocomposite material has an $IC_{50}$ value of 24.76 μg/mL in an in-vitro cellular viability assay.

EXAMPLES

The following examples demonstrate a method of treating cancer. The examples are provided solely for illustration and are not to be construed as limitations of the present disclosure, as many variations thereof are possible without departing from the spirit and scope of the present disclosure.

Example 1: Fabricating Calcium Silicate ($CaSiO_3$)

Equal moles of calcium nitrate ($Ca(NO_3)_2$) and sodium metasilicate ($Ca_2O_4Si$) were dispersed in 100 milliliters (mL) of ethanol:water (1:1) in a 150 mL glass beaker and sonicated for 15 minutes (min). The mixture was transferred to a 200 mL autoclave and then placed in an oven operated at 180 degrees Celsius (° C.) for 2.0 hours (h). The product was dispersed in 500 mL of distilled water with an ultrasonic bath for 10 min, filtered via a Buchner system, rinsed with distilled water, and dried at 120° C. for 1.0 h.

Example 2: Fabricating Graphitic Carbon Nitride (g-$C_3N_4$)

About 30.0 grams (g) of urea was placed in a 250 mL porcelain crucible, covered with its porcelain cover, then the hall crucible and cover were wrapped with three layers of aluminum foil to reduce the urea loss of evaporation. The crucible was heated via a furnace set at 600° C. for 45 min.

Example 3: Fabricating the $Cu_2(OH)_2NO_3/CaSiO_3/$ g-$C_3N_4$ 2.0 g of $CaSiO_3$, 2.0 g of g-$C_3N_4$ and the amount of copper (II) nitrate ($Cu(NO_3)_2·H_2O$) enough to produce 2.0 g of copper hydroxide nitrate ($Cu_2(OH)_2NO_3$) were transferred to a mono wave-200 vial (G30), dispersed in 20 mL ethylene glycol monomethyl ether via an ultrasonic bath for 30 min. The vial was closed with its teflon cover and placed in the Anton-Baar Monowave-200 operated at 180° C. and 5.0 bar pressure for 1 h. The product was dispersed in 1 liter (L) distilled water with an ultrasonic bath for 30 min, filtered via a Buchner system, rinsed with distilled water, and dried at 150° C. for 2.0 h.

Example 4: Anticancer Activity

Cell line Propagation: The cells were grown on RPMI-1640 medium supplemented with 10% inactivated fetal calf serum and 50 µg/mL gentamycin. The cells were maintained at 37° C. in a humidified atmosphere with 5% $CO_2$ and were sub-cultured two to three times a week.

Example 5: Cytotoxicity Evaluation Using Viability Assay

For antitumor assays, the tumor cell lines were suspended in a medium at concentration $5 \times 10^4$ cell/well in Corning 96-well tissue culture plates, then incubated for 24 h. The tested compounds were then added into 96-well plates (three replicates) to achieve ten concentrations for each compound. Six vehicle controls with media were run for each 96-well plate as a control. After incubating for 24 h, the numbers of viable cells were determined by the MTT test. Briefly, the media was removed from the 96 well plates and replaced with 100 microliters (µL) of fresh culture RPMI 1640 medium without phenol red, then 10 µL of the 12 millimolar (mM) MTT stock solution (5 mg of MTT in 1 mL of phosphate buffer saline (PBS)) was added to each well, including the untreated controls. The 96-well plates were incubated at 37° C. and 5% $CO_2$ for 4 h. An 85 µL aliquot of the media was removed from the wells, and 50 µL of DMSO was added to each well, mixed thoroughly with the pipette, and then incubated at 37° C. for 10 min. Then, after, the optical density was measured at 590 nanometers (nm) with the microplate reader (Sunrise, TECAN, Inc., USA) to determine the number of viable cells. The percentage of viability was calculated as $[(OD_t/OD_c)] \times 100\%$, where $OD_t$ is the mean optical density of wells treated with the tested sample. $OD_c$ is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

Figure 2:
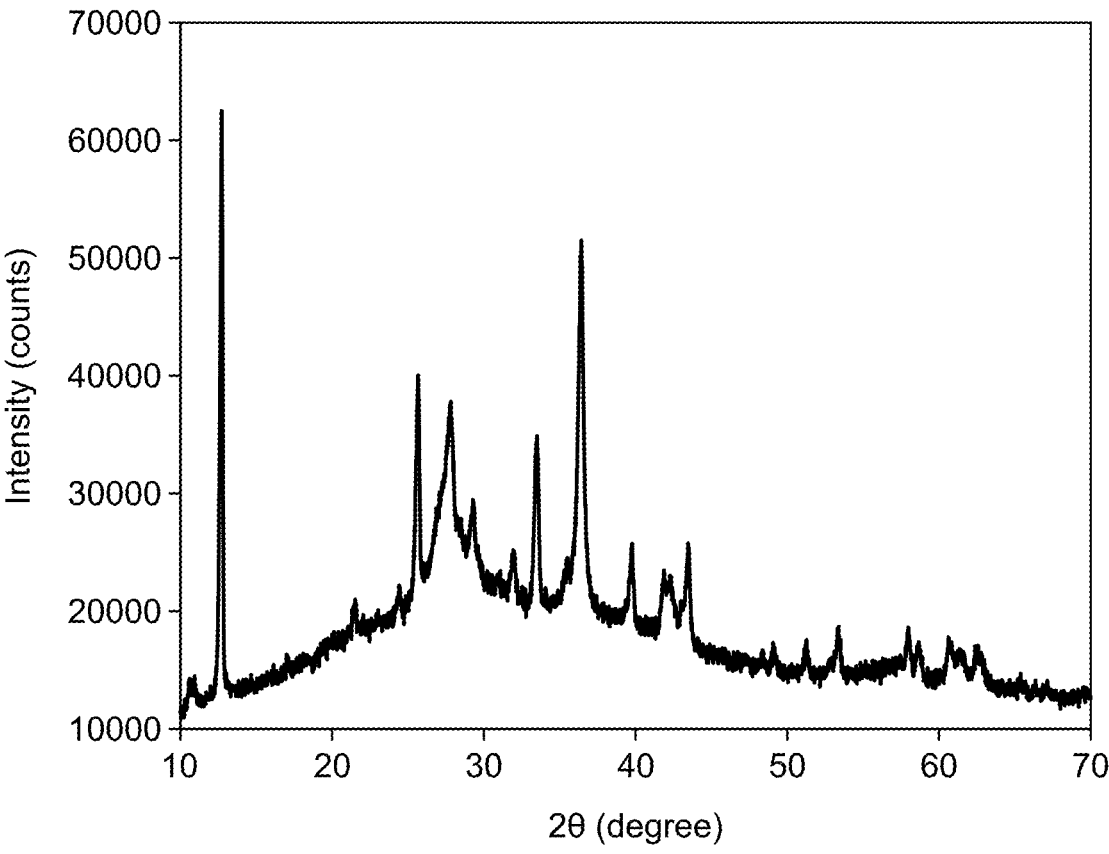
FIG. 2 shows a X-ray diffraction (XRD) diffractogram of the $Cu_2(OH)_2NO_3/CaSiO_3@g$-$C_3N_4$ nanocomposite, according to certain embodiments.

The crystallinity and phases identification present in $Cu_2(OH)_2NO_3/CaSiO_3@g-C_3N_4$ nanocomposite was analyzed by X-ray diffraction (XRD) and the results are given in FIG. 2. The intense peaks and high intensity values indicate that the powder is highly crystalline in nature. In addition, the peak broadening indicates the small particle size of the prepared composites.

Examination of the diffraction patterns with the standard JCPDS cards reveals the presence of metallic nanosheet of $Cu_2(OH)_2NO_3$ as a major phase together with minor phases of copper (I) oxide ($Cu_2O$), $CaSiO_3$, and $g-C_3N_4$. The $Cu_2(OH)_2NO_3$ phase was indexed to the strong reflections at $2\theta$ values of 12.9°, 25.7°, 33.8°, 36.7°, and 43.4° (JCPDS No. 00-003-0061). The $CaSiO_3$ monoclinic phase (JCPDS No. 00-001-0720) was detected at $2\theta$ values of 27.3°, 32.3° and 62.6°. The $Cu_2O$ was characterized by a strong reflection at $2\theta$ value of 36.4° (JCPDS No. 01-078-2076). The diffractions related to $g-C_3N_4$ was observed at 33.2°, and 58.0° (COD No. 1534042 and JCPDS No. 00-050-0848). The weak diffractions of both $CaSiO_3$ and $g-C_3N_4$ may be attributed to the semi-crystalline nature of these phases and the high crystallinity of $Cu_2O$ and $Cu_2(OH)_2NO_3$ phases in the prepared composite. No other phases were detected, indicating the successful fabrication of $Cu_2(OH)_2NO_3/CaSiO_3@g-C_3N_4$.

Transmission electron microscopy (TEM) images of $Cu_2(OH)_2NO_3/CaSiO_3/g-C_3N_4$ nanocomposite were presented in FIG. 3A-B. The TEM images showed that two-dimensional porous structure constructed with curled and wrinkled nanosheets and platelets of the $g-C_3N_4$ (FIG. 3A). The image shows also well dispersion of rodsof metal oxides nanoparticles with a size 1.97 m and some aggregates on nanosheets of $g-C_3N_4$. The corresponding selected area electron diffraction (SAED) pattern reveals diffraction spots with interplanar spacing of 0.365 nm, 0.242 nm, 0.141 nm, and 0.124 nm due to ($CaSiO_3$: 2-12, $Cu_2(NO_3)(OH)_3$: −111), ($CaSiO_3$: −2-12, $Cu_2(NO_3)(OH)_3$: −211), ($CaSiO_3$: 322, $Cu_2(NO_3)$ $(OH)_3$: 00-5), and ($CaSiO_3$: −125) diffraction planes (FIG. 3C).

Figure 4A:
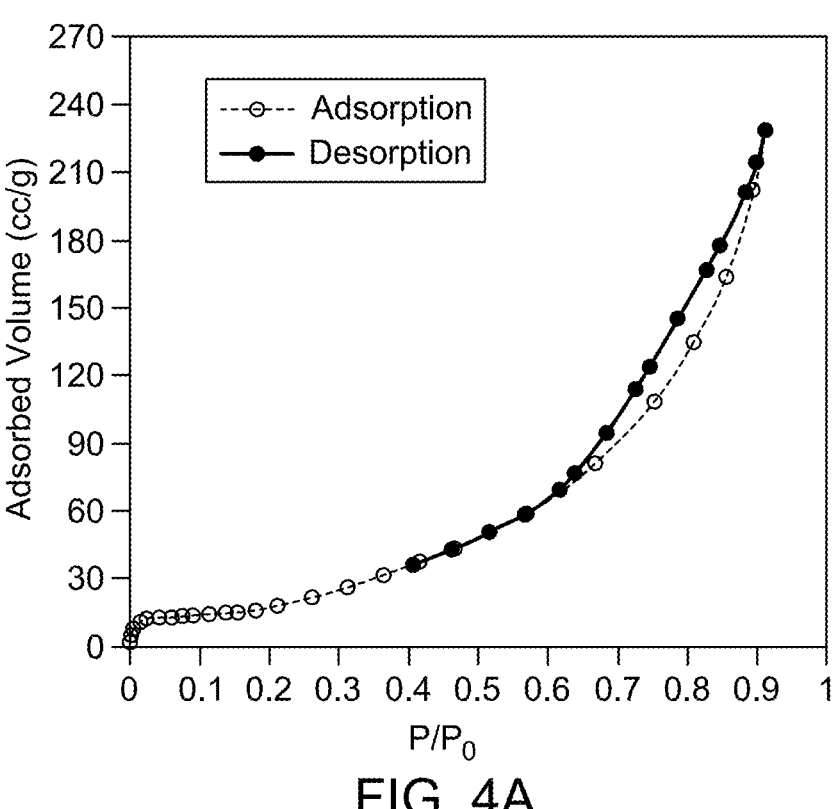
FIG. 4A shows a graph depicting adsorption-desorption isotherms of the $Cu_2(OH)_2NO_3/CaSiO_3@g$-$C_3N_4$ nanocomposite, according to certain embodiments.
Figure 4B:
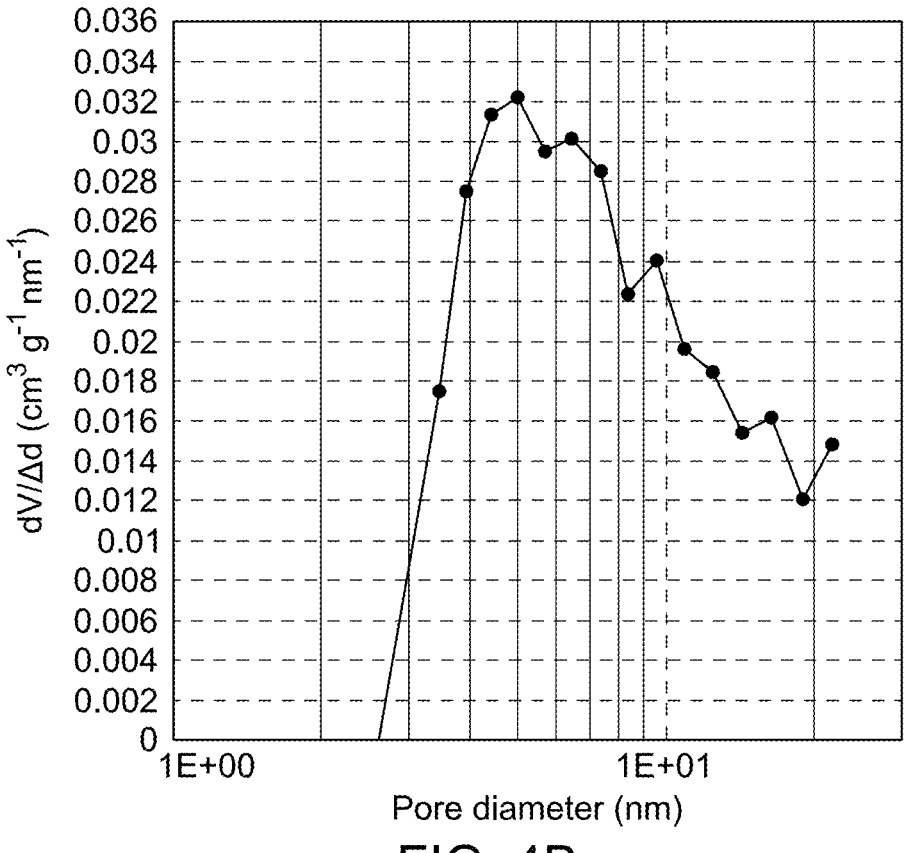
FIG. 4B shows a graph depicting the pore size distribution of the $Cu_2(OH)_2NO_3/CaSiO_3@g$-$C_3N_4$ nanocomposite, according to certain embodiments.

FIG. 4A displays the nitrogen adsorption-desorption isotherms of $Cu_2(OH)_2NO_3/CaSiO_3@g-C_3N_4$ nanocomposite. The nitrogen sorption isotherm of the composite is belonging to type IV with noticed hysteresis loop, indicating the formation of mesoporous structures. However, shifting the loop to a relatively higher pressure ($P/P_0=0.62-1$) suggests the presence of wide mesopores, which may result from the deposition of metal oxides particles in the wide pores of $g-C_3N_4$. Furthermore, the Brunauer-Emmett-Teller (BET) surface area of the $Cu_2(OH)_2NO_3/CaSiO_3@g-C_3N_4$ sample was calculated to be 149.9 square meters per gram ($m^2 \ g^{-1}$). The marked high specific surface area reflects the good dispersion of these metal oxides nanoparticles on $g-C_3N_4$. and $CaSiO_3$. Moreover, the pore size distribution curves, plotted using the Barrett-Joyner-Halenda (BJH) method, for the $Cu_2(OH)_2NO_3/CaSiO_3@g-C_3N_4$ sample exhibited unimodal distribution with average pore diameters maximized at 5 nanomters (nm) and pore volume of 0.354 cubic centimeters per gram ($cm^3 \ g^{-1}$). All the isotherms belong to the category H3 type of pores, which do not exhibit limiting adsorption at high $P/P_0$, and arise due to aggregation of plate-like particles giving rise to slit-shaped pores (FIG. 4B). This indicates that the assembly of $Cu_2(OH)_2NO_3/CaSiO_3@g-C_3N_4$ composite provoked a mesoporous structure.

Figure 5:
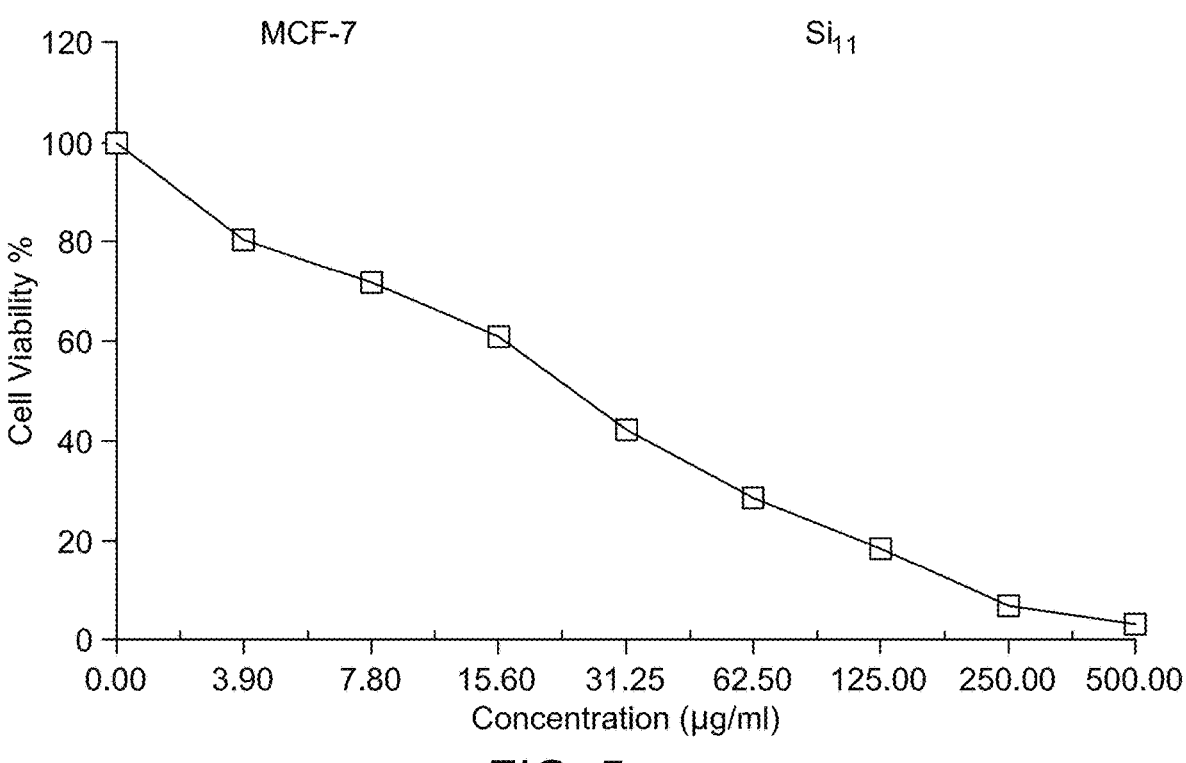
FIG. 5 is a graph depicting the inhibitory activity of the $Cu_2(OH)_2NO_3/CaSiO_3/g$-$C_3N_4$ nanocomposite against the MCF-7 cell line, according to certain embodiments.
Figure 6:
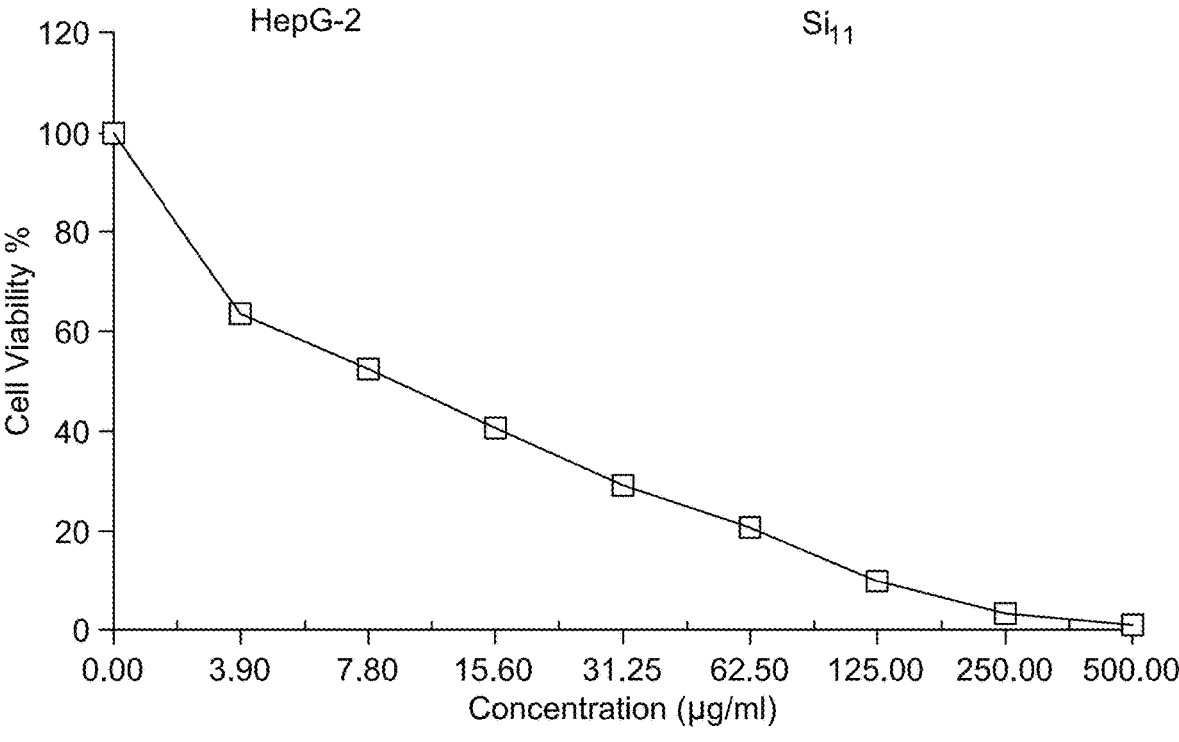
FIG. 6 is a graph depicting the inhibitory activity of the $Cu_2(OH)_2NO_3/CaSiO_3/g$-$C_3N_4$ nanocomposite against the HepG-2 cell line, according to certain embodiments.

An in-vitro investigation was conducted for the the $Cu_2(OH)_2NO_3/CaSiO_3/g-C_3N_4$ against the Human Hepatocellular Carcinoma (HepG-2) and Human Breast Carcinoma cell lines (MCF-7). A concentration range of 3.0 to 500 g/mL $Cu_2(OH)_2NO_3/CaSiO_3/g-C_3N_4$ and the obtained results against the MCF-7 cell line are illustrated in FIG. 5. The MCF-7 cells' viability started declining with only 3.9 g/mL $Cu_2(OH)_2NO_3/CaSiO_3/g-C_3N_4$ dose, the $IC_{50}$ was 24.76 µg/mL, and the maximum dose (500 g/mL) showed a 96.94% inhibition of the MCF-7. Furthermore, the exact concentration range of 3.0 to 500 g/mL $Cu_2(OH)_2NO_3/CaSiO_3/g-C_3N_4$ was applied against the HepG-2 cell line, and the obtained results are illustrated in FIG. 6. The HepG-2 cells' viability started declining with only 3.9 g/mL $Cu_2(OH)_2NO_3/CaSiO_3/g-C_3N_4$ dose. The $IC_{50}$ was 9.42 µg/mL, and the maximum dose (500 g/mL) showed a 99.03% inhibition of the HepG-2.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of in vitro inhibiting cancer cell growth, comprising:
   contacting a $Cu_2(OH)_3NO_3/CaSiO_3@g-C_3N_4$ nanocomposite with a cancer cell,
   wherein the cancer cell is from a cell line selected from a group consisting of a human hepatocellular carcinoma (HepG-2) cell line and a human breast carcinoma (MCF-7) cell line; thereby
   inhibiting the cancer cell growth.

2. The method of claim 1, further comprising:

contacting the cancer cell with the $Cu_2(OH)_3NO_3/$ $CaSiO_3@g\text{-}C_3N_4$ nanocomposite at a concentration of 3 µg/mL to 500 µg/mL.

3. The method of claim 1, wherein the $Cu_2(OH)_3NO_3/$ $CaSiO_3@g\text{-}C_3N_4$ nanocomposite comprises:

a graphite-phase carbon nitride (g-$C_3N_4$) in an amount of 20 to 40 percent by weight (wt. %), and a copper hydroxide nitrate ($Cu_2(OH)_3NO_3$) in an amount of 20 to 40 wt. %, and a calcium silicate ($CaSiO_3$) in an amount of 20 to 40 wt. %, based on a total weight of the $Cu_2(OH)_3NO_3/CaSiO_3@g\text{-}$ $C_3N_4$ nanocomposite.

4. The method of claim 1, wherein the cell line is the HepG-2 cell line, and wherein the $Cu_2(OH)_3NO_3/CaSiO_3@g\text{-}C_3N_4$ nanocomposite has a half-maximal inhibitory concentration ($IC_{50}$) value of 5 to 15 µg/mL.

5. The method of claim 1, wherein the cell line is the MCF-7 cell line, and wherein the $Cu_2(OH)_3NO_3/CaSiO_3@g\text{-}C_3N_4$ nanocomposite has a half-maximal inhibitory concentration ($IC_{50}$) value of 20 to 30 µg/mL.

6. The method of claim 1, wherein the $Cu_2(OH)_3NO_3/$ $CaSiO_3@g\text{-}C_3N_4$ nanocomposite is made by a process comprising:

mixing a calcium silicate ($CaSiO_3$), a graphite-phase carbon nitride (g-$C_3N_4$), and a copper salt in a glycol solvent to form a mixture;

microwaving the mixture to form the $Cu_2(OH)_3NO_3/$ $CaSiO_3@g\text{-}C_3N_4$ nanocomposite.

7. The method of claim 6, further comprising:

forming the $CaSiO_3$ by sonicating a mixture of a calcium salt and a silicate salt in an aqueous alcohol solution to form a calcium silicate mixture, followed by heating the calcium silicate mixture to a temperature of 160 to 200° C. for 1 to 3 hours to form the $CaSiO_3$, wherein the calcium salt is selected from a group consisting of calcium nitrate, calcium chloride, calcium phosphate, calcium carbonate and calcium citrate, and wherein the silicate salt is selected from a group consisting of calcium silicate, sodium silicate, potassium silicate, zeolites and micas.

8. The method of claim 6, further comprising:

forming the g-$C_3N_4$ by heating urea to a temperature of 550 to 650° C. for 30 to 60 minutes.

9. The method of claim 6, wherein the mixing comprises a copper salt selected from a group consisting of copper nitrate, copper chloride, copper sulfate, copper bromide and copper cyanide.

10. The method of claim 6, wherein the microwaving is performed at a temperature of 160 to 200° C. at a pressure of 4 to 6 bar for 30 to 90 minutes.

11. The method of claim 1, wherein the $Cu_2(OH)_3NO_3/$ $CaSiO_3@g\text{-}C_3N_4$ nanocomposite comprise a plurality of metal oxides nanorods and a plurality of g-$C_3N_4$ nanosheets.

12. The method of claim 1, wherein the $Cu_2(OH)_3NO_3/$ $CaSiO_3@g\text{-}C_3N_4$ nanocomposite has the metal oxide nanorods comprising $Cu_2(OH)_3NO_3$ and $CaSiO_3$.

13. The method of claim 1, wherein the $Cu_2(OH)_3NO_3/$ $CaSiO_3@g\text{-}C_3N_4$ nanocomposite has the metal oxide nanorods of an average length 1 to 3 µm.

14. The method of claim 1, wherein the $Cu_2(OH)_3NO_3/$ $CaSiO_3@g\text{-}C_3N_4$ nanocomposite has the metal oxide nanorods comprising nanowires protruding perpendicularly to the rods.

15. The method of claim 1, wherein the $Cu_2(OH)_3NO_3/$ $CaSiO_3@g\text{-}C_3N_4$ nanocomposite has the metal oxide nanorods comprising nanowires of a length 10 to 50 nm dispersed on the g-$C_3N_4$ nanosheets with some aggregates of the metal oxide nanorods.

16. The method of claim 1, wherein the $Cu_2(OH)_3NO_3/$ $CaSiO_3@g\text{-}C_3N_4$ nanocomposite has a mesoporous structure with a plurality of wide pores in the g-$C_3N_4$ nanosheets where the metal oxides nanorods deposit.

17. The method of claim 1, wherein $Cu_2(OH)_3NO_3/$ $CaSiO_3@g\text{-}C_3N_4$ nanocomposite has an average pore diameter of 3 to 7 nm.

18. The method of claim 1, wherein the $Cu_2(OH)_3NO_3/$ $CaSiO_3@g\text{-}C_3N_4$ nanocomposite has a Brunauer-Emmett-Teller (BET) surface area of 140 to 160 $m^2\cdot g^{-1}$.

19. The method of claim 1, wherein the $Cu_2(OH)_3NO_3/$ $CaSiO_3@g\text{-}C_3N_4$ nanocomposite has an average pore volume of 0.3 to 0.4 $cm^3\cdot g^{-1}$.

* * * * *